(12) United States Patent
Sekoguchi et al.

(10) Patent No.: US 7,254,006 B2
(45) Date of Patent: Aug. 7, 2007

(54) ION GENERATING ELEMENT AND ION GENERATOR, AIR CONDITIONING APPARATUS, CLEANER AND REFRIGERATOR CONTAINING THE SAME

(75) Inventors: Yoshinori Sekoguchi, Nara (JP); Masahito Yamamoto, Nara (JP); Mamoru Morikawa, Yamatokooriyama (JP)

(73) Assignee: Sharp Kabushiki Kaisha, Osaka (JP)

( * ) Notice: Subject to any disclaimer, the term of this patent is extended or adjusted under 35 U.S.C. 154(b) by 132 days.

(21) Appl. No.: 10/485,987

(22) PCT Filed: Aug. 7, 2002

(86) PCT No.: PCT/JP02/08106

§ 371 (c)(1),
(2), (4) Date: Feb. 5, 2004

(87) PCT Pub. No.: WO03/013620

PCT Pub. Date: Feb. 20, 2003

(65) Prior Publication Data

US 2004/0253417 A1    Dec. 16, 2004

(30) Foreign Application Priority Data

Aug. 7, 2001    (JP)    ............................. 2001-239908

(51) Int. Cl.
*H01T 23/00* (2006.01)
(52) U.S. Cl. ...................... 361/230; 361/231
(58) Field of Classification Search ................ 361/230, 361/231; 96/97
See application file for complete search history.

(56) References Cited

U.S. PATENT DOCUMENTS

| 3,070,971 | A | * | 1/1963 | Jacobs ........................... 62/78 |
| 4,155,093 | A | * | 5/1979 | Fotland et al. .............. 347/127 |
| 5,227,192 | A | | 7/1993 | Asano et al. |
| 6,024,930 | A | | 2/2000 | Racca et al. |
| 6,494,934 | B2 | * | 12/2002 | Fukushima ..................... 95/63 |
| 6,576,909 | B2 | * | 6/2003 | Donaldson et al. ......... 250/426 |

FOREIGN PATENT DOCUMENTS

| DE | 44 20 038 A1 | 1/1995 |
| JP | 60-160661 U | 10/1985 |
| JP | 62-240979 A | 10/1987 |
| JP | 6-318490 A | 11/1994 |

(Continued)

*Primary Examiner*—Burton S. Mullins
*Assistant Examiner*—Ann T. Hoang
(74) *Attorney, Agent, or Firm*—Birch, Stewart, Kolasch & Birch, LLP (57) ABSTRACT

An inner electrode formed inside a dielectric body and a surface electrode formed on a surface of the dielectric body. The surface electrode is formed in a grid pattern with pointed parts formed inside the grid section. Each pointed part is in the shape of a triangle whose vertices are two arbitrary points on a side of the grid section and an arbitrary point inside the grid section, or a quadrangle whose vertices are a crossing of grid lines, an arbitrary point near a straight line connecting crossings of grid lines in the diagonal positions, and two arbitrary points on sides of the grid section. An ion generating element is formed which can generate positive ions and negative ions. The ion generator can be used in an air conditioning apparatus, cleaner or refrigerator.

10 Claims, 11 Drawing Sheets

FOREIGN PATENT DOCUMENTS

| | | |
|---|---|---|
| JP | 07-144016 | 6/1995 |
| JP | 7-95477 B2 | 10/1995 |
| JP | 9-7735 A | 1/1997 |
| JP | 10-231104 A | 9/1998 |
| JP | 10-241828 A | 9/1998 |
| JP | 2001-166118 A | 6/2001 |
| JP | 2002-65838 A | 3/2002 |

* cited by examiner

ION GENERATING ELEMENT AND ION GENERATOR, AIR CONDITIONING APPARATUS, CLEANER AND REFRIGERATOR CONTAINING THE SAME

BACKGROUND OF THE INVENTION

1. Field of the Invention

The present invention relates to an ion generating element capable of emitting both of positive ions and negative ions into a space and disinfecting bacteria floating in the air, an ion generator using the ion generating element, an air conditioning apparatus, cleaner and refrigerator using the ion generator. The present invention more particularly relates to an ion generating element capable of emitting positive ions and negative ions in a stable manner, reducing noise caused by the emission of ions, and decreasing the emission of ozone by designing a surface electrode formed on a surface of a dielectric body to have a special shape.

2. Description of the Related Art

In general, in a closed room which is ventilated less frequently, such as an office and a conference room, when there are many people in the room, the air polluting substances such as carbon dioxide discharged by breathing, smoke of cigarettes and dust increase, and consequently negative ions which have the effect of relaxing human are reduced in the air. Sometimes a large amount of negative ions are lost by cigarette smoke particularly and the negative ions are reduced to about ½ to ⅕ of the usual amount.

Therefore, a number of ion generators have been sold in the market to supply negative ions into the air, but all the generators just generate only negative ions by a DC high voltage system. Such a conventional ion generator for generating only negative ions can supply negative ions into the air, but can not positively remove the floating bacteria in the air.

The present inventors eagerly studied and, as a result, have invented a structure of emitting $H^+(H_2O)_n$ (n is a natural number) as positive ions and $O_2^-(H_2O)_m$ (m is a natural number) to enclose the floating bacteria in the air with the ions, make a chemical reaction, and disinfect the floating bacteria in the air by the decomposition function of hydrogen peroxide ($H_2O_2$) and/or hydroxyl radical (·OH) that are active species generated in the chemical reaction.

Figure 10:
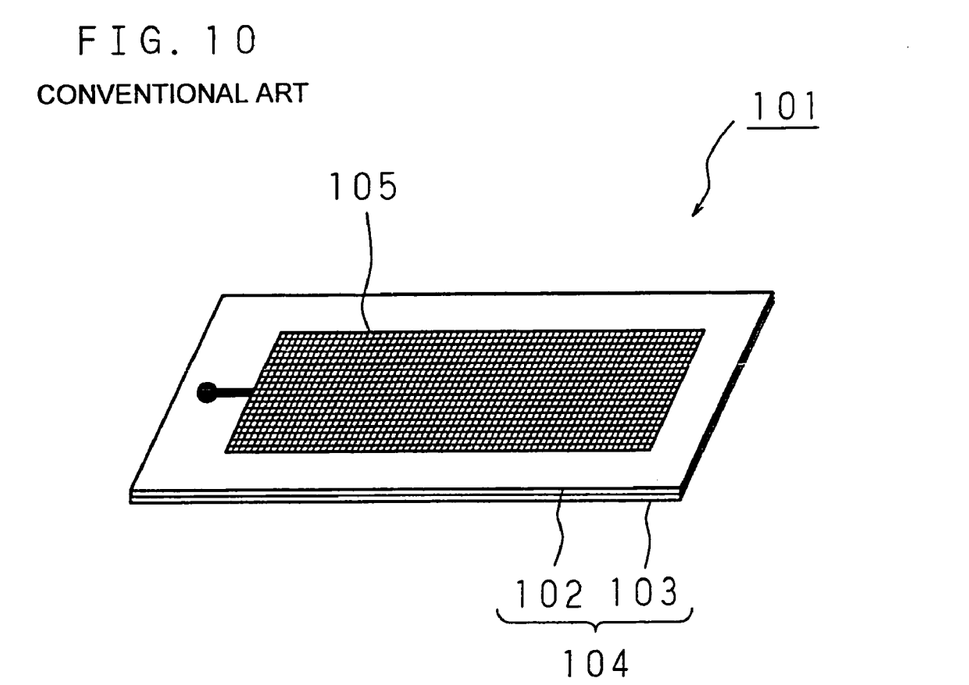
FIG. 10 is a perspective view showing a conventional ion generating element.
Figure 11:
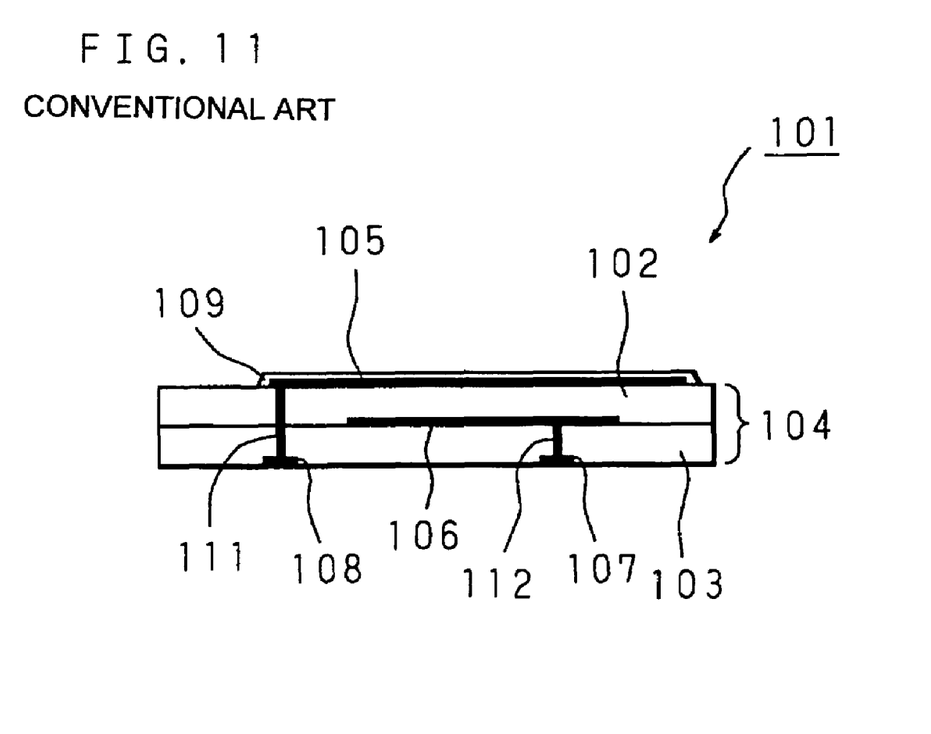
FIG. 11 is a cross sectional view of the conventional ion generating element.

The applicant of the present application proposed in Japanese Patent Application No. 2001-166118 an ion generating element comprising a surface electrode formed on a surface of a dielectric body, and an inner electrode provided in parallel to the surface electrode inside the dielectric body. FIG. 10 is a perspective view showing the ion generating element, and FIG. 11 is a cross sectional view of the ion generating element. As shown in these figures, a dielectric body 104 made of ceramics is composed of an upper dielectric body 102 and a lower dielectric body 103, and a strip-like inner electrode 106 is formed between the upper dielectric body 102 and the lower dielectric body 103.

On the other hand, on a surface of the upper dielectric body 102, a surface electrode 105 is formed in parallel to the inner electrode 106. The surface electrode 105 is screen-printed using tungsten, on the upper dielectric body 102, and also formed in a grid pattern as shown in FIG. 10 so as to emit a large amount of positive ions and negative ions into the air. In short, the grid-like surface electrode 105 is formed on a surface of the dielectric body 102 by screen printing so as to efficiently generate positive ion and negative ions.

In addition, the ion generating element 101 comprises: a coating layer 109, made of alumina or the like, covering the surfaces of the dielectric body 102 and surface electrode 105; a surface electrode connecting part 111 whose one end is connected to the surface electrode 105 and the other end is connected to a surface electrode contact 108 provided on the lower face of the lower dielectric body 103; and an inner electrode conducting part 112 whose one end is connected to the inner electrode 106 and the other end is connected to an inner electrode contact 107 provided on the lower face of the lower dielectric body 103. By connecting the inner electrode contact 107 and the surface electrode contact 108 to a voltage applying circuit, not shown, and applying an AC voltage to the inner electrode 106 and the surface electrode 105 formed in a grid pattern on a surface of the upper dielectric body 102, a large amount of positive ions and negative ions are generated.

In the ion generating element proposed in Japanese Patent Application No. 2001-166118, however, it is necessary to take a voltage fluctuation during the actual use into account and apply a voltage for satisfactory generation of ions. In other words, the relation between the voltage and ion generation has characteristics that ions are generated by application of a voltage equal to or higher than a certain value and the amount of ions increases with an increase in the voltage, but the ion increase rate decreases when a higher voltage is applied. In a stable region, there is a problem of big discharge sound on the electrode surface, and it is necessary to decrease noise as small as possible in actual application.

Furthermore, since ozone harmful to human body is generated with the generation of ions, it is necessary to decrease the generation of ozone as low as possible while maintaining the emission of ions.

The inventors of the present application conducted experiments repeatedly by changing the conditions of the surface electrode formed on a surface of the dielectric body, and found that it was possible to generate ions from a lower voltage region and generate ions in a stable manner in a wide range of applied voltage by further extending the grid-like surface electrode to form a pointed surface electrode inside the grid squares. Accordingly, since stable ion generation is performed even at a low voltage, the inventors also found that it was possible to reduce noise and the generation of ozone by optimizing the shape and size of the surface electrode.

The present invention has been made based on the findings and with the aim of solving the above problems, and it is an object of the present invention to provide an ion generator capable of generating positive ions and negative ions in a stable manner under a wide range of applied voltage while reducing noise and also capable of reducing the generation of ozone, by forming the surface electrode in a special shape, and to provide an ion generator using the ion generating element.

Moreover, it is another object of the present invention to provide an air conditioning apparatus capable of being incorporated in various apparatuses such as an air conditioner, a microwave oven and a washing/drying machine by using the ion generator of the present invention and a blower for sending ions generated by the ion generator to the outside.

Furthermore, it is still another object of the present invention to provide a cleaner and a refrigerator, capable of effectively reducing dirt in air such as dust generated during cleaning and unpleasant smells in the refrigerator, by installing the ion generator of the present invention and a blower for sending the generated ions out of the cleaner or into the refrigerator.

BRIEF SUMMARY OF THE INVENTION

An ion generating element according to the present invention comprises: a dielectric body; an inner electrode formed inside the dielectric body; and a surface electrode formed on a surface of the dielectric body, and is characterized in that the surface electrode is formed in a grid pattern and has a pointed part in each grid square.

The ion generating element according to the present invention wherein the pointed part is made of a triangle whose vertices are two arbitrary points on a side of the grid square and an arbitrary point inside the grid square.

The ion generating element according to the present invention wherein a plurality of the triangles are formed for each grid square, and the distance between the vertices of the triangles inside the grid square is not less than 0.25 mm but not more than 0.5 mm.

The ion generating element according to the present invention wherein the pointed part is made of a quadrangle whose vertices are a crossing of grid lines, an arbitrary point near a straight line connecting crossings of grid lines in diagonal positions, and two arbitrary points on sides of the grid square.

The ion generating element according to the present invention wherein the pitch of the grid is not less than 1.0 mm but not more than 1.5 mm.

The ion generating element according to the present invention comprises: a plate-like dielectric body; an inner electrode formed inside the dielectric body; and a surface electrode formed on a surface of the dielectric body, wherein the inner electrode lies inside the extent of the surface electrode.

An ion generator according to the present invention comprises: an ion generating element of the present invention; and a voltage applying circuit for applying a voltage to the surface electrode and the inner electrode of the ion generating element, wherein $H^+(H_2O)_n$(n is a natural number) and $O_2^-(H_2O)_m$(m is a natural number) are generated in the air by application of a voltage by the voltage applying circuit.

An air conditioning apparatus according to the present invention comprising an ion generator of the present invention, and a blower for sending ions generated by the ion generator to the outside.

A cleaner according to the present invention comprising an ion generator of the present invention, and a blower for emitting ions generated by the ion generator out of the cleaner.

A refrigerator according to the present invention comprising an ion generator of the present invention, and a blower for emitting ions generated by the ion generator into the refrigerator.

According to the present invention, on a surface of the dielectric body, in addition to the grid-like surface electrode, the pointed surface electrode is formed inside the grid squares. More specifically, a triangle having two arbitrary points on a side of a grid square and an arbitrary point inside the grid square as the vertices, or a quadrangle having a crossing of grid lines, an arbitrary point near a straight line connecting crossings of grid lines in the diagonal positions, and two arbitrary points on sides of the grid square as the vertices is formed as an extended part. Thus, by further providing the surface electrode with the pointed parts, it is possible to generate positive ions and negative ions in a stable manner in a wide range of voltage application. Accordingly, ion generation at a low voltage becomes possible, and noise and the generation of ozone can be effectively reduced by decreasing the voltage. Since the present invention can generate ions in a stable manner without particularly depending on the strength of the applied voltage, the ion generating element of the present invention can be incorporated in numerous apparatuses regardless of the types of apparatuses and conditions of use such as home use or business use.

DETAILED DESCRIPTION OF THE INVENTION

The following description will explain the present invention in detail with reference to the drawings illustrating some embodiments thereof.

Figure 1:
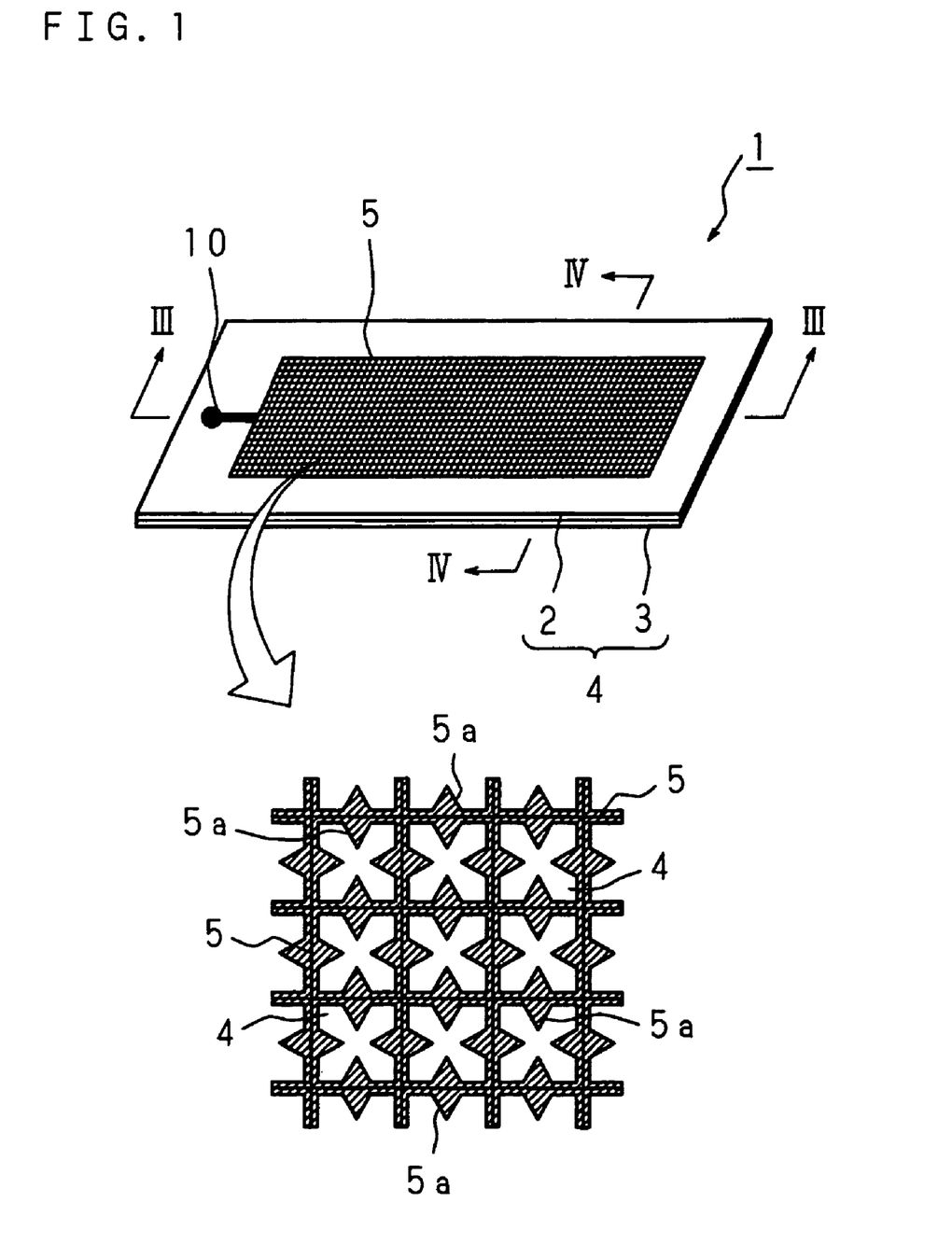
FIG. 1 is a schematic perspective view showing the structure of an ion generating element according to the present invention and the configuration of a surface electrode by enlargement.
Figure 2:
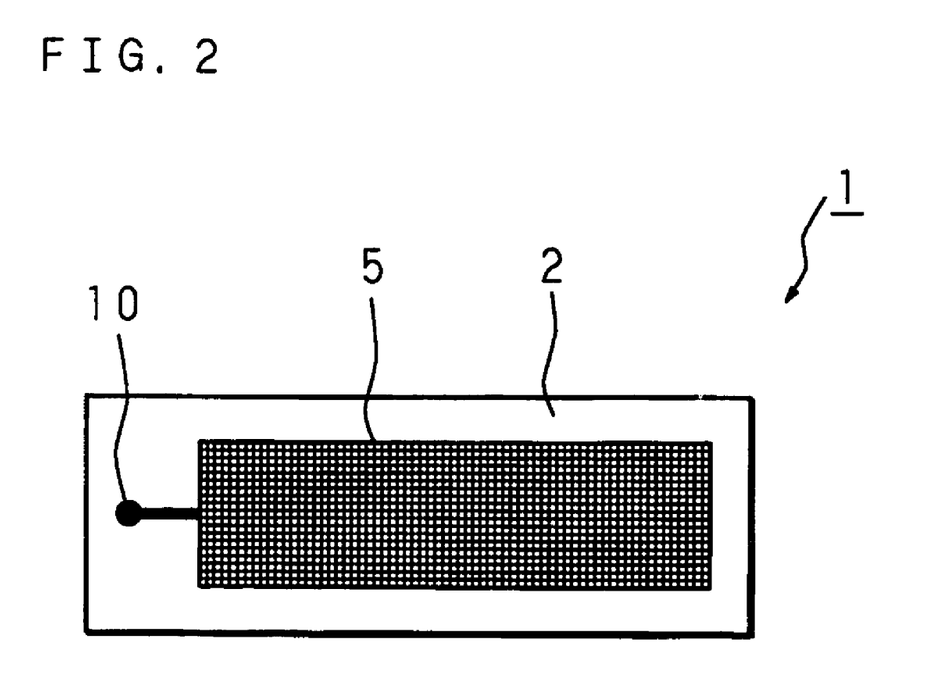
FIG. 2 is a plan view of the ion generating element.
Figure 3:
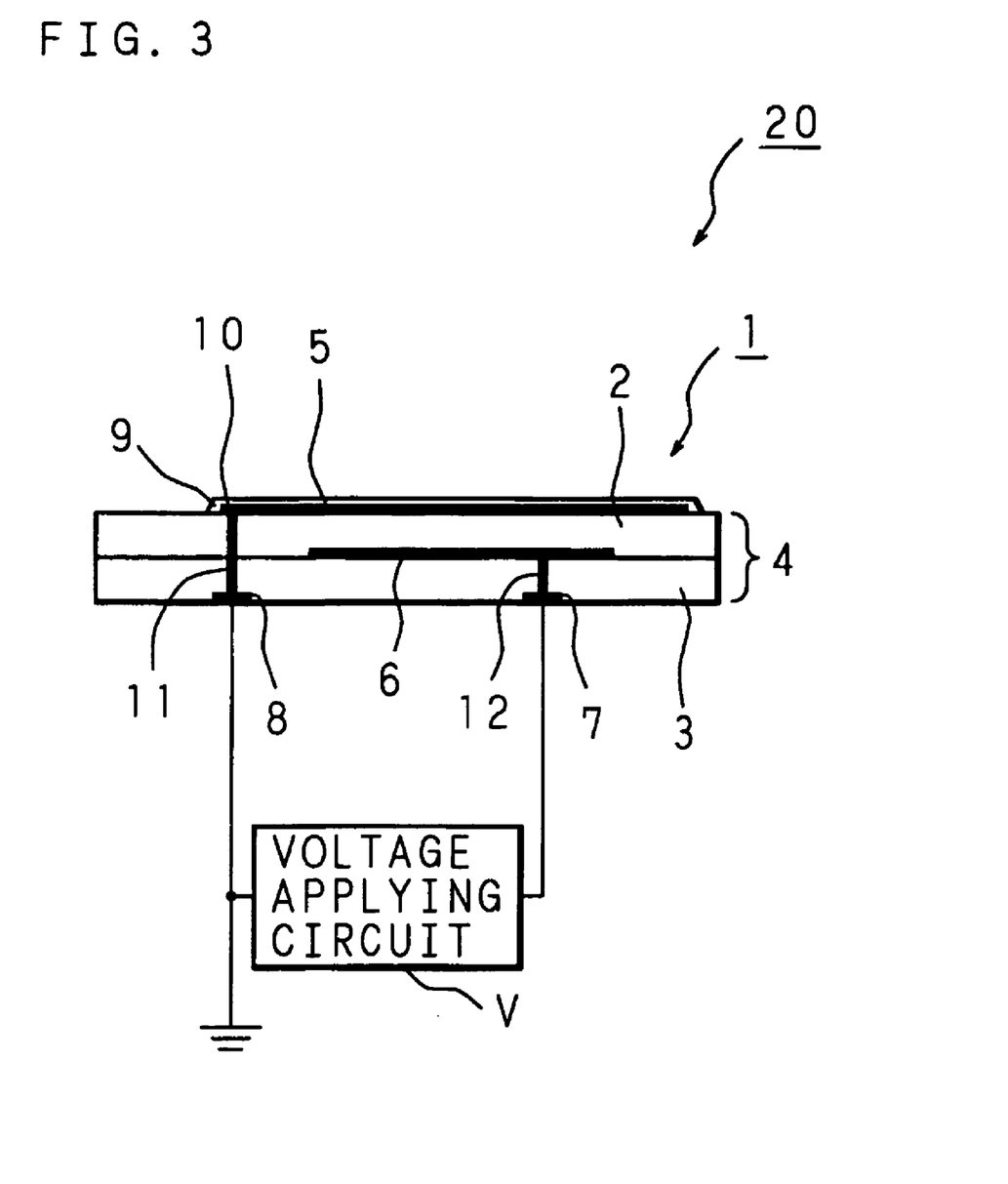
FIG. 3 is a cross sectional view cut along the III—III line of FIG. 1.
Figure 4:
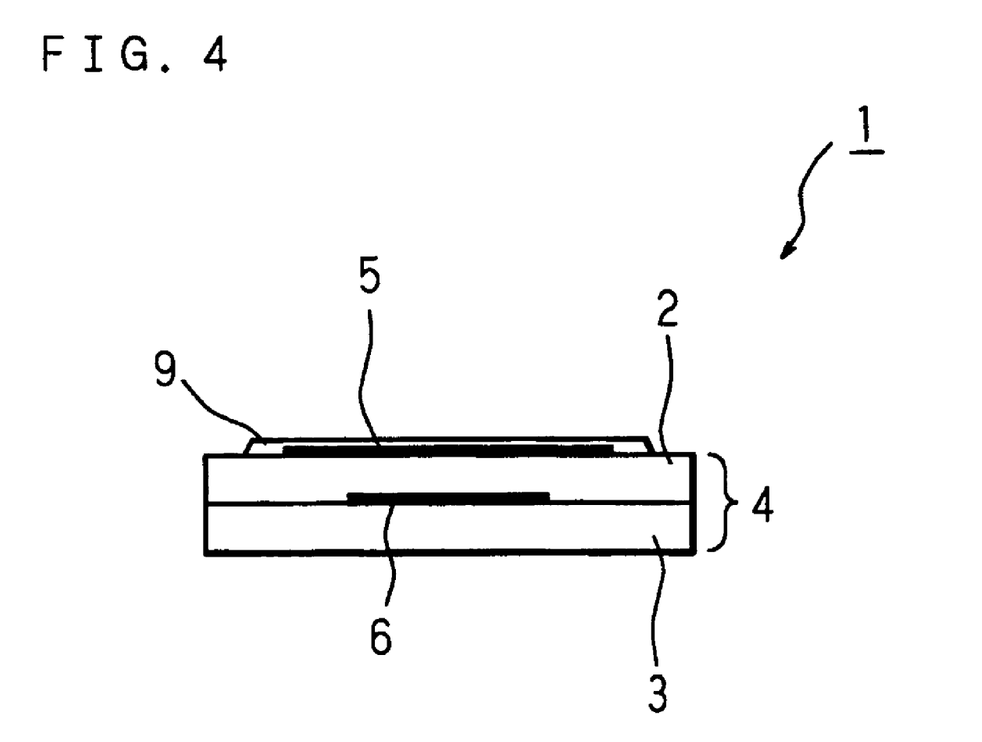
FIG. 4 is a cross sectional view cut along the IV—IV line of FIG. 1.

FIG. 1 is a schematic perspective view showing the structure of an ion generating element according to the present invention and the configuration of a surface electrode by enlargement; FIG. 2 is a plan view of the ion generating element; FIG. 3 is a cross sectional view cut along the III—III line of FIG. 1; and FIG. 4 is a cross sectional view cut along the IV—IV line of FIG. 1.

An ion generating element 1 of the present invention comprises: a surface electrode 5 formed on a surface of a plate-like dielectric body 4, in a grid pattern with pointed parts 5a formed in the grid squares (a structure including the grid part and the pointed parts 5a will be hereinafter referred to as the surface electrode 5); a surface electrode contact 8, provided on the lower face of the dielectric body 4, for supplying electric power to the surface electrode 5; a strip like inner electrode 6 buried inside the dielectric body 4 so as to be substantially parallel to the surface electrode 5; and an inner electrode contact 7, provided on the lower face of the dielectric body 4 for supplying electric power to the inner electrode 6. Note that the dielectric body 4 is composed of an upper dielectric body 2 and a lower dielectric body 3.

The following description will explain each structure in detail. An organic material having an excellent oxidation resistance is suitable for the material of the dielectric body 4, and, for example, it is possible to use a resin such as polyimide and glass epoxy. In the case where an inorganic material is to be used, it is possible to use ceramics such as high purity alumina, crystallized glass, forsterite and steatite. When the corrosion resistance is taken into consideration, inorganic materials are preferred. When the moldability and the later-described easiness in constructing the electrode are taken into consideration, it is suitable to use ceramics for molding. Since it is desirable to have a uniform insulating resistance between the surface electrode 5 and the inner electrode 6, material with a low internal density and the dielectric body 4 with a uniform insulation rate are more preferred.

The dielectric body 4 can have a circular, oval or other shape including a polygon shape, or even have a cylindrical shape. However, when the productivity is taken into consideration, it is preferred that the dielectric body 4 is in the form of a plate as shown in the drawing. Although the material for the surface electrode 5 is not particularly limited as long as it has conductivity, but the material needs to satisfy a condition that it does not cause deformation such as melting by discharge. In this embodiment, the surface electrode 5 is formed by screen-printing tungsten on a surface of the dielectric body 4. Note that, when the surface electrode 5 is formed so as to protrude from the surface of the dielectric body 4, it is preferred that the protruding section has a uniform thickness. On the other hand, when the surface electrode 5 is formed on the inner electrode 6 side than the surface of the dielectric body 4, it is preferred that the depth thereof is uniform.

Figure 5:
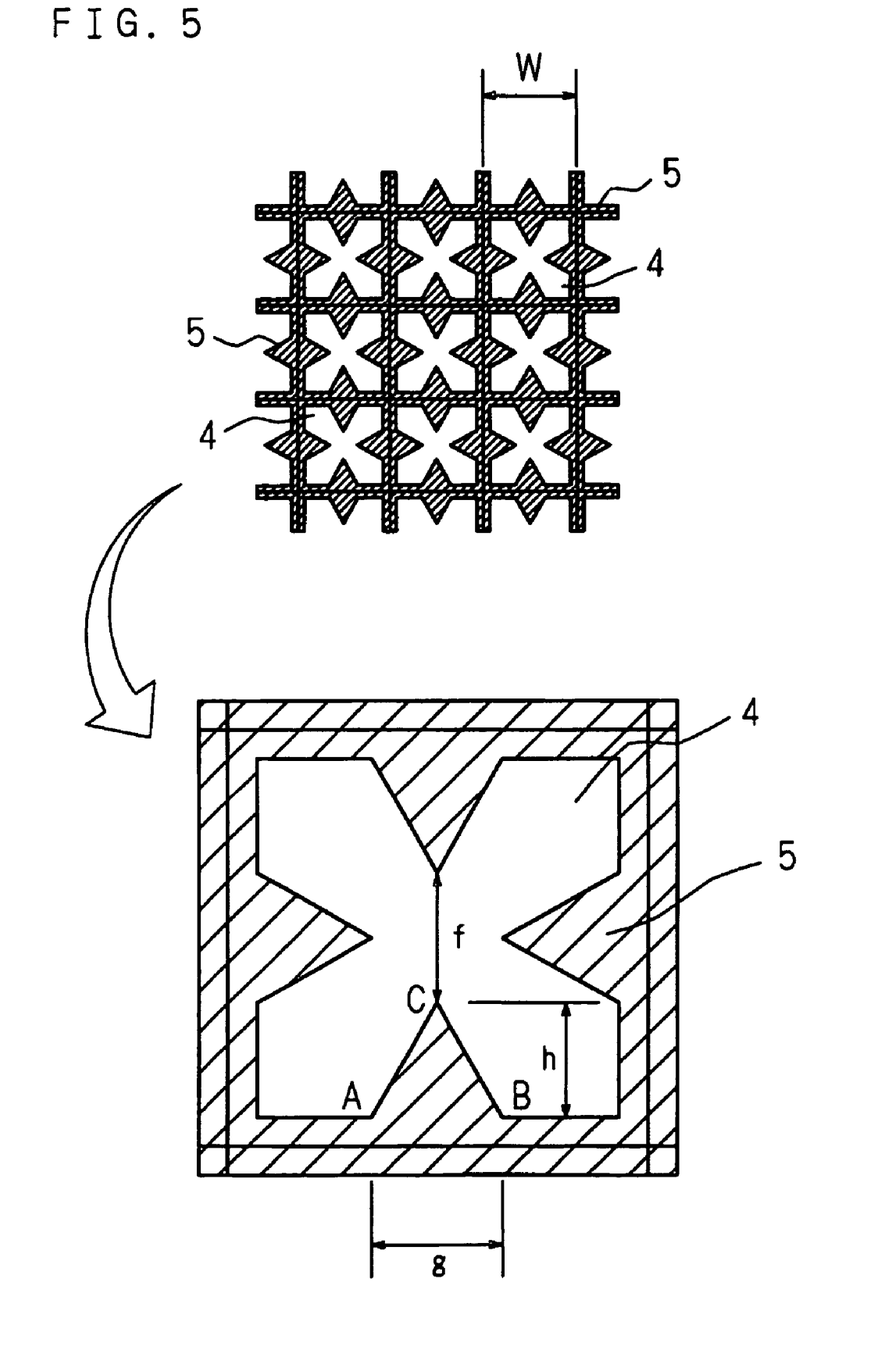
FIG. 5 is an enlarged view showing the detail of the surface electrode.

As shown in FIG. 1, the surface electrode 5 is formed in a grid pattern and further has pointed parts extended in the inward direction of the grid squares. FIG. 5 is an enlarged view showing the detail of the surface electrode 5. As shown in FIG. 5, the pitch (w) of the grid of the surface electrode 5 is not less than 1.0 mm but not more than 1.5 mm, and preferably 1.2 mm. The extended pointed part is in the shape of a triangle drawn by connecting two arbitrary points (point A and point B) on a side of the grid square and an arbitrary point C inside the grid square. A distance g between the point A and the point B is about 0.25 mm to 0.45 mm, and a height h of the triangle (the length of a perpendicular dropped from the point C to a straight line connecting the point A and the point B) is preferably 0.25 mm to 0.35 mm. Similarly, a distance f between the vertices (between a point C and a point C) of the triangles inside the grid square is not less than 0.25 mm but not more than 0.5 mm, and more preferably 0.35 mm. Note that the propriety of the above-mentioned values is examined by the later-described experiments.

Moreover, although this embodiment is explained on the assumption that the point A and the point B of the triangle are located in the approximately center section of a side of the grid square and the triangle is an equilateral triangle or an isosceles triangle with the point C as the vertex, the triangle is not necessarily limited to such a shape, the positions of the point A and point B can be located in any position on a side of the grid square as long as the extended part has a pointed shape, and the triangle can be a scalene triangle.

Figure 6:
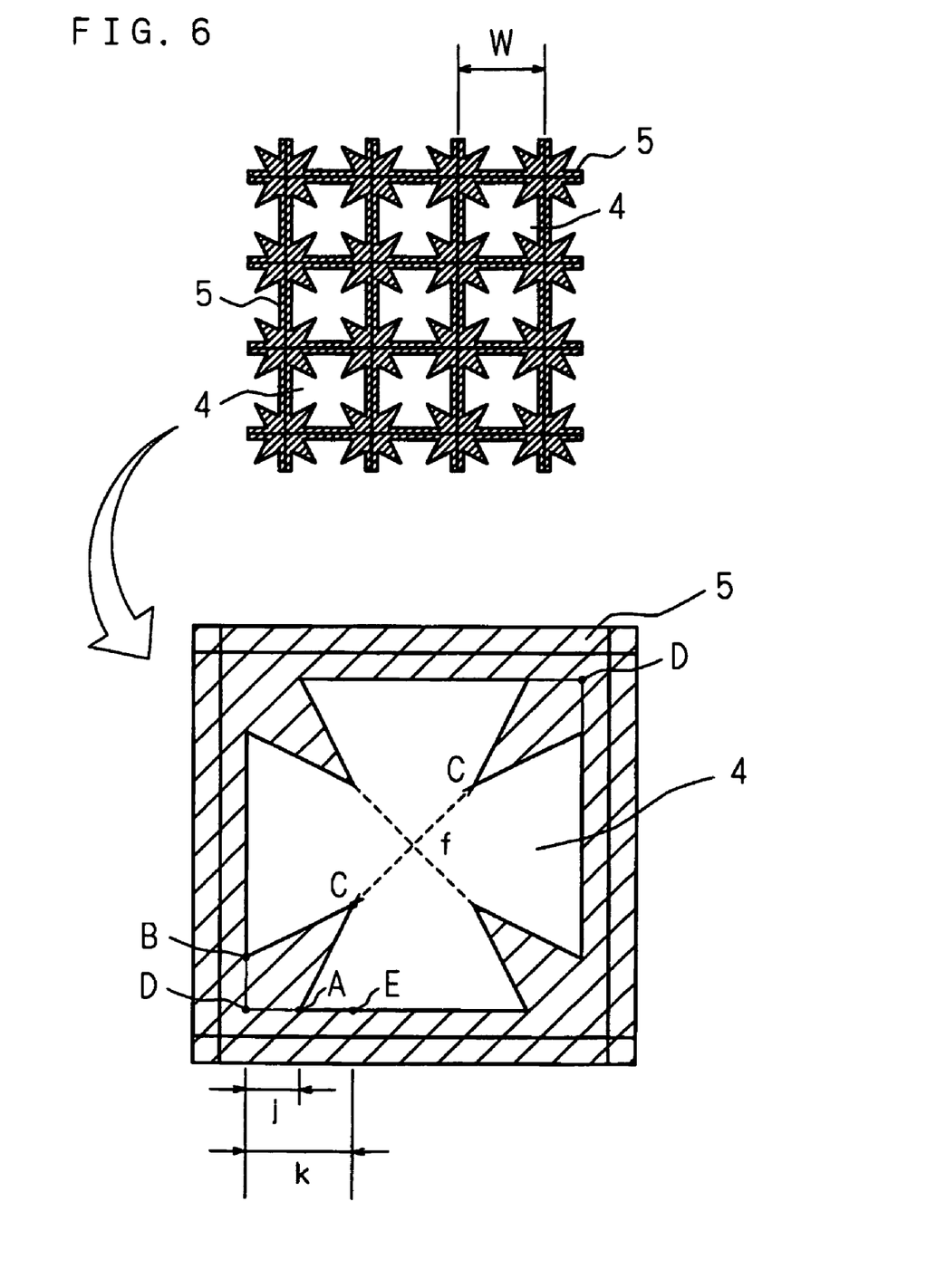
FIG. 6 is an explanatory view showing another embodiment of the surface electrode.

FIG. 6 is an explanatory view showing another embodiment of the surface electrode 5. As another pointed shape, it is possible to use a quadrangle whose vertices are a crossing D of grid lines, an arbitrary point C near a straight line connecting the crossings D and D in the diagonal positions, and two arbitrary points (point A and point B) on sides of the grid square. Like the above-mentioned triangular shape, the distance f between the vertices (between a point C and a point C) inside the grid square is not less than 0.25 mm but not more than 0.5 mm, and more preferably 0.35 mm. A distance j between the point A and the point D and a distance j between the point B and the point D are both preferably about 0.15 mm, and a distance k between the point D and a point E at which a perpendicular line dropped from the point C to a side the grid square crosses the side is preferably about 0.3 mm.

Figure 7:
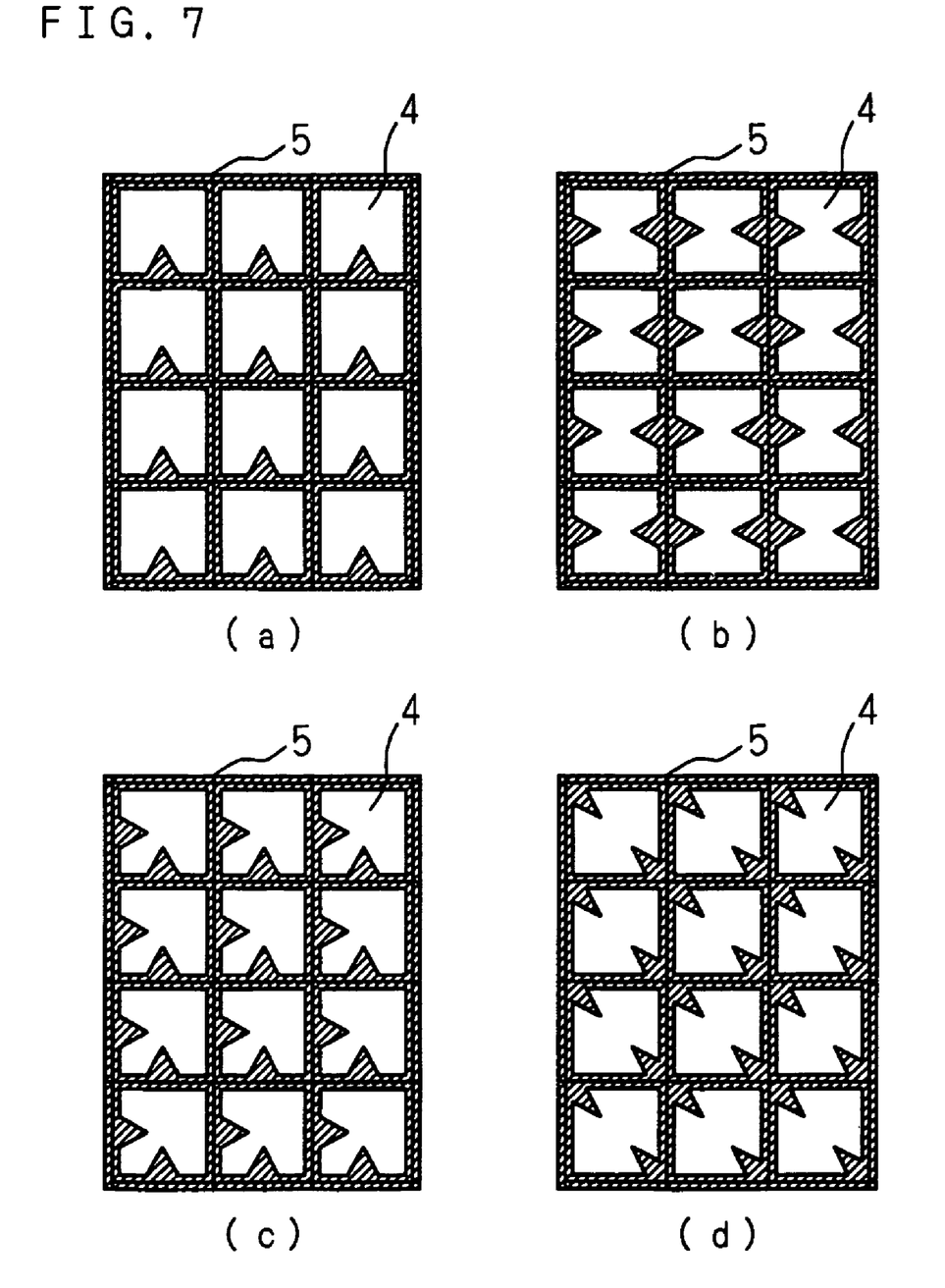
FIGS. 7(a)–(d) is an explanatory views showing still other embodiments of the surface electrode.

FIGS. 7(a)-(d) are explanatory views showing still another embodiment of the surface electrode 5. As shown in FIGS. 7(a)-(d), it is not necessary to provide the pointed triangle on all the sides of the grid squares, and the pointed triangles may be provided on only one side as shown in FIG. 7(a), on two sides to face each other as shown in FIG. 7(b), or on two adjacent sides of each grid square as shown in FIG. 7(c). Although not shown, needless to say, the extended triangles may be formed on three sides of each grid square, except for one side. Similarly, the number of quadrangles can be 1, 2, 3 or 4, and as shown in FIG. 7(d), pointed quadrangles may be formed in two diagonal positions.

Next, referring to FIG. 1 through FIG. 4, the following description will explain the inner electrode 6. For the inner electrode 6, it is possible to use a material having conductivity such as tungsten, for example, and the inner electrode 6 is formed in a strip form on a surface of the upper dielectric body 2 or the lower dielectric body 3. As shown in FIG. 3, the inner electrode 6 is formed between the upper dielectric body 2 and the lower dielectric body 3. In particular, when the insulation resistance between the surface electrode 5 and the inner electrode 6 is uniform, since the discharge state is stable and positive ions and negative ions can be generated in a stable manner, it is desirable that the surface electrode 5 and the inner electrode 6 be parallel to each other. In other words, the inner electrode 6 is positioned inside the dielectric body 4 so that the inner electrode 6 faces and is parallel to the surface electrode 5 and that the distance between the surface electrode 5 and the inner electrode 6 (the interelectrode distance) is uniform.

The surface electrode contact 8 shown in FIG. 3 is a contact connected to the surface electrode 5, and the surface electrode 5 and other construction are connected by connecting one end of a lead wire made of copper, aluminum or the like to this contact and connecting the other end to a contact of the other construction. Since the surface electrode contact 8 and the lead wire are easily connected, the surface electrode contact 8 can be provided at any position as long as it is on a surface of the dielectric body 4. However, the surface electrode contact 8 will have the same electric potential as the surface electrode 5, it is desirable that the distance between the inner electrode 6 and the surface electrode contact 8 be longer than the interelectrode distance. By satisfying this desirable relationship, a stable discharge state can be obtained.

The inner electrode contact 7 is a contact connected to the inner electrode 6, and the inner electrode 6 and other construction are connected by connecting one end of a lead wire made of copper, aluminum or the like to this contact and connecting the other end to a contact of the other construction. Since the inner electrode contact 7 and the lead wire are easily connected, the inner electrode contact 7 can be provided at any position as long as it is on a surface of the dielectric body 4. However, since the inner electrode contact 7 will have the same electric potential as the inner electrode 6, it is desirable that the distance between the surface electrode 5 and the inner electrode contact 7 be longer than the interelectrode distance. By satisfying this desirable relationship, a stable discharge state can be obtained.

Moreover, the distance between the surface electrode contact 8 and the inner electrode contact 7 are made longer than the interelectrode distance. Further, when the surface electrode contact 8 and the inner electrode contact 7 are both provided on a surface (lower face) facing a surface (upper face) where the surface electrode 5 are formed, wires such as lead wires are not laid on the upper face where positive ions and negative ions are generated. Therefore, if a blower is additionally provided to send air to the surface where the surface electrode 5 is formed, the flow of air will never be disturbed by the lead wires, and thus this arrangement is preferable. Similarly, such an effect can also be obtained by providing the surface electrode contact 8 and the inner electrode contact 7 at positions other than on the upper face.

Note that the above-mentioned "other construction" means voltage applying means or the ground, and there is a case where a voltage is applied by connecting the surface electrode 5 and the inner electrode 6 to a voltage applying circuit V (see FIG. 3).

In this case, when the surface electrode 5 is connected to the ground to have a ground potential and the internal electrode 6 is connected to the voltage applying circuit V, a high voltage is not applied to the exposed surface electrode 5, and thereby preventing electric shock accidents. FIG. 3 shows an example of such a construction, in which an ion generator 20 is composed of the ion generating element 1 and the voltage applying circuit V.

In order to generate both positive ions and negative ions with a single ion generating element 1, the voltage applied between the surface electrode 5 and the inner electrode 6 by the voltage applying circuit V needs to be an alternating voltage. This alternating voltage is not limited to a sinusoidal alternating voltage that is generally used for commercial power supply (hereinafter the sinusoidal alternating voltage will be referred to as the "AC voltage"), and a rectangular alternating voltage may be applied, or the alternating voltage may be applied using another waveform.

The ion generator 20 according to the present invention can function as an air conditioning apparatus 30 by further incorporating a blower therein. This air conditioning apparatus 30 is used in a space, for example, in a home, a ward and operation room of a hospital, a vehicle, an air plane, a warehouse, a refrigerator, and a machine, and is applied, for example, to an air conditioner, a dehumidifier, a humidifier, an air purifier, a refrigerator, a fan heater, a microwave oven, a washing/drying machine, a cleaner, and a disinfecting apparatus.

Figure 8:
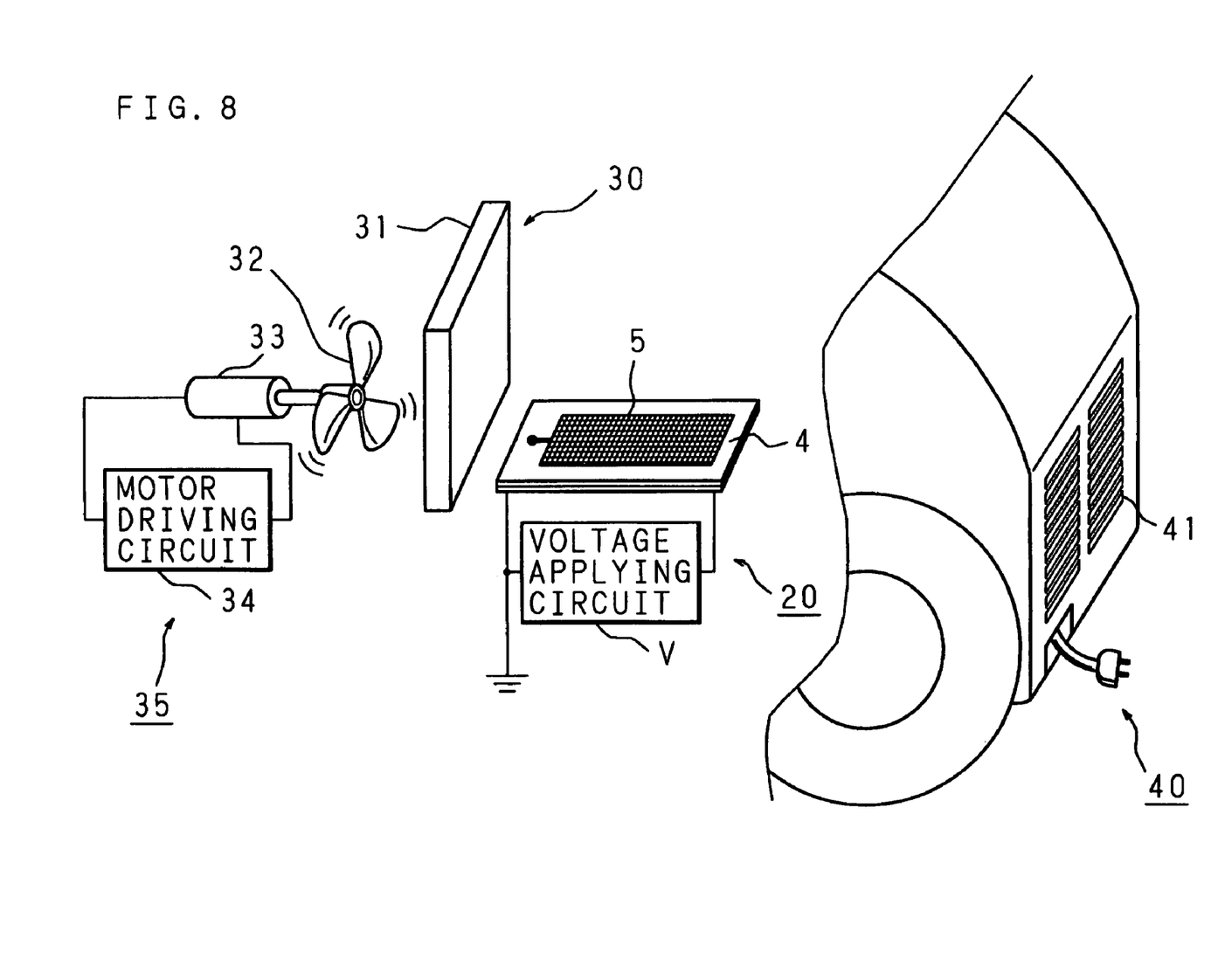
FIG. 8 is a schematic diagram showing the essential section of a cleaner using an air conditioning apparatus.

FIG. 8 is a schematic diagram showing the essential section of a cleaner 40 using the air conditioning apparatus 30. As shown in FIG. 8, the discharge air which is generated by the suction of air with the cleaner 40 is discharged from external discharge openings 41 of the cleaner 40 via a filter 31 for removing particulates, by a blower 35 composed of a motor 33 connected to a motor driving circuit 34 and a fan 32 connected to the rotation axis of the motor 33.

The air conditioning apparatus 30 according to the present invention comprises the blower 35 and the ion generator 20 disposed close to each other. The motor driving circuit 34 and the voltage applying circuit V are supplied with a voltage in a synchronized manner by a controller, not shown, and the ion generator 20 generates a large amount of $H_+(H_2O)_n$ and $O_2^-(H_2O)_m$ inside the cleaner 40. Meanwhile, the blower 35 spreads the positive ions and negative ions generated inside the cleaner 40 into the room space being cleaned, through the external discharge openings 41 by the air blown from the fan 32. With this structure, it is possible to effectively remove dirt in the air generated by the cleaner 40 and dirt in the air caused by the cleaning action.

Figure 9:
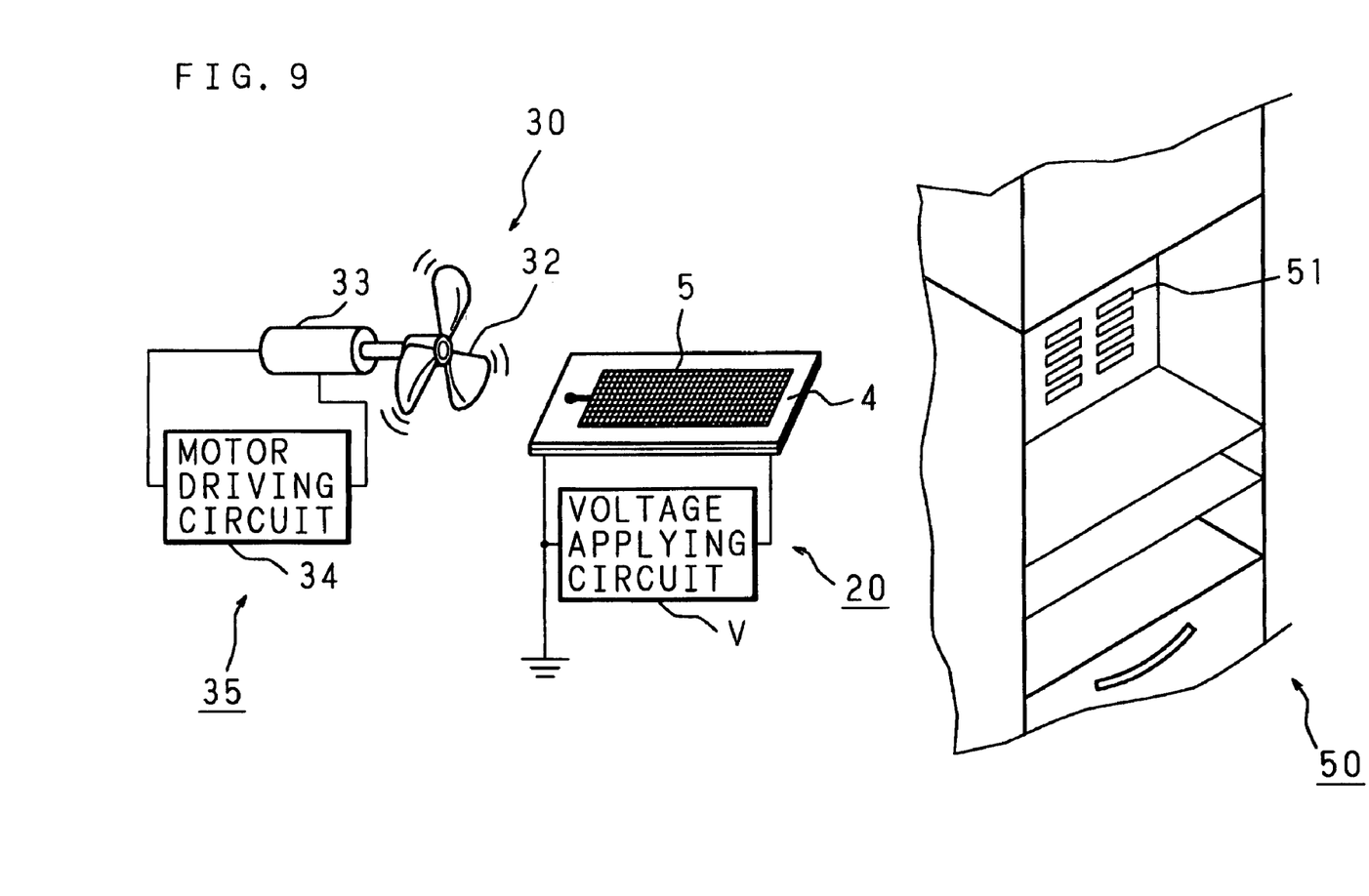
FIG. 9 is a schematic diagram showing the essential section in a refrigerator using an air conditioning apparatus.

FIG. 9 is a schematic diagram showing the essential section inside a refrigerator 50 using the air conditioning apparatus 30. Like the cleaner 40 illustrated in FIG. 8, the residual contaminated air is discharged from internal openings 51 of the refrigerator 50 by the blower 35 composed of the motor 33 connected to the motor driving circuit 34 and the fan 32 connected to the rotation axis of the motor 33.

A voltage is applied to the motor driving circuit 34 and the voltage applying circuit V by a controller, not shown, with a timing programmed in advance in a ROM, not shown, in the controller. Then, the ion generator 20 generates a large amount of $H^+(H_2O)_n$ and $O_2^{-(H}2O)_m$. Meanwhile, the blower 35 spreads the generated positive ions and negative ions into the space inside the refrigerator 50 through the internal openings 51 by the air blown from the fan 32. With this structure, it is possible to effectively remove the unpleasant smells generated by the matters cooled in the refrigerator.

Now, referring to FIG. 1 through FIG. 4, the following description will explain a more specific embodiment. The dielectric body 4 of the ion generating element 1 according this embodiment has a rectangular parallelepiped shape with a width of 15 mm, a length of 37 mm and a thickness of 0.9 mm, and is provided with the strip-like internal electrode 6 which has a size of about 6 mm×24 mm and is formed in parallel to the upper face of the dielectric body 4, and the surface electrode 5 which has a width of about 10.8 mm and a length of 27.6 mm and is arranged so that the center line (the III—III line in FIG. 1) connecting the centers of both end lines (about 15 mm-wide side) on the upper face of the dielectric body 4 is the line of symmetry. The surface electrode 5 is formed so that if the surface electrode 5 is projected onto the internal electrode 6, the projection of the surface electrode 5 spreads to an area outside the internal electrode 6, and, if the surface electrode 5 is virtually present on a plane where the internal electrode 6 is formed (in the plan view), a portion corresponding to the periphery of the surface electrode 5 is located outside a portion corresponding to the periphery of the inner electrode 6. By forming the surface electrode 5 in such a manner, when discharge is performed from the inner electrode 6 to the surface electrode 5, the discharge is carried out inside the surface electrode 5, and therefore the discharge state in the air is stable and ions can be generated in a good balance. Note that the shapes and sizes of the grid and pointed triangle, quadrangle, etc. of the surface electrode 5 are the same as those mentioned above.

Moreover, the surface electrode contact 8 is provided on the lower face of the dielectric body 4. The surface electrode contact 8 is connected to the surface electrode 5 by an upper-face connecting part 10 having one end connected to the surface electrode 5 and the other end at a position on the upper face of the dielectric body 4 facing the surface electrode contact 8 and a length longer than the interelectrode distance and by a surface electrode connecting part 11 for connecting the other end of the upper-face connecting part 10 to the surface electrode contact 8.

Further, the inner electrode contact 7 is provided at an arbitrary position on the lower face of the dielectric body 4, facing the inner electrode 6. The inner electrode contact 7 is connected to the inner electrode 6 by an inner electrode connecting part 12. Note that the distance between the surface electrode contact 8 and the inner electrode contact 7 is made longer than the interelectrode distance.

Next, a method for manufacturing the ion generating element 1 is explained. First, a 0.45 mm-thick high-purity alumina sheet is cut into a predetermined size (15 mm width×37 mm length) so as to form two alumina bases having substantially the same size. Note that, alumina with a purity equal to or higher than 90% can be used, and alumina with a purity of 92% is used here.

The surface electrode 5 and the upper face connecting part 10 are integrally formed by screen-printing tungsten in a grid pattern on the upper face of one of the two alumina bases so as to fabricate the upper dielectric body 2. Then, tungsten is screen-printed in a strip pattern on the upper face of the other alumina base to form the inner electrode 6 integrally on the surface of the alumina base, and the surface electrode contact 8 and the inner electrode contact 7 are formed on the lower face of the alumina base by screen printing, thereby fabricating the lower dielectric body 3.

Further, an alumina coating layer 9 (only shown in FIG. 3) is formed on a surface of the upper dielectric body 2 so as to provide the surface electrode 5 with an insulation coat. After placing the lower face of the upper dielectric body 2 and the upper face of the lower dielectric body 3 one upon another, pressure bonding and vacuum suction are performed, and then they are placed in a furnace and baked under a non-oxidation atmosphere at 1400° C. to 1600° C. According to this manufacturing process, it is possible to easily manufacture the ion generating element 1 shown in the present invention.

Next, the following description will explain an example in which a voltage was applied to the ion generating element 1 formed by the above-mentioned method. In order to apply a voltage between the surface electrode 5 and the internal electrode 6 of the ion generating element 1, the ion generator 20 is constructed by connecting the voltage applying circuit V and the surface electrode contact 8 with a lead wire, and connecting the inner electrode contact 7 and the voltage applying circuit V with a lead wire. Then, by operating the voltage applying circuit V to apply an AC high voltage between the surface electrode 5 and the inner electrode 6, positive ions and negative ions are generated.

The following description will explain experiments which were performed by changing the shape of the surface electrode 5 so as to examine the influence of the change in the shape on the yields of ions, noise, and the amount of ozone. Prototypes (2) and (3) were produced by extending the surface electrode 5 to have a triangular configuration (see FIG. 5). In the prototype (2), the width g was 0.45 mm and the height h was 0.45 mm, while, in the prototype (3), the width g was 0.35 mm and the height h was 0.3 mm. A prototype (7) had a conventional simple grid-like configuration, and the grid pitch was 0.8 mm. The applied voltage to the voltage applying circuit V was 70 to 90V, the potential difference between the peaks of the AC voltage was about 5.0 to 6.3 kV, and the frequency was about 40 kHz. The yield of positive ions, the yield of negative ions, the amount of ozone, and the noise value were measured under the above-mentioned conditions. The results are shown in Table 1a, 1b (set forth hereinafter).

Note that the measurement of the yields of ions was performed at a measuring point about 25 cm apart from the ion generating element 1, and the measurement of the noise value was carried out at a measuring point about 11.5 cm apart from the ion generating element 1 in a noiseless room. Moreover, the inner electrode 6 was made to have a uniform strip form with a size of about 6 mm×24 mm, and the width of lines forming the grid of the surface electrode 5 was made 0.25 mm in this experiment. Note that the "pitch" means the distance between the center line of one side of a grid square and the center line of another side of the grid square.

As is clear from Table 1b, it was confirmed that the prototypes (2) and (3) generated ions in a more stable manner compared to the prototype (7) not only when the input voltage was high, but when the input voltage was low. Thus, by forming the grid-like surface electrode 5 to have further extended pointed parts, it is possible to generate ions in a stable manner with a wide range of voltage. Moreover, although noise increases with an increase in the yields of ions, since the prototypes (2) and (3) can be used with a low voltage as is clear from Table 1b, it is possible to limit noise. Furthermore, it was possible to significantly reduce the generation of ozone harmful to human body.

Next, prototypes (1), (4) and (5) were manufactured by changing the grid pitch, the width g, the height h and the distance f between the vertices of triangles (see FIG. 5), and similar experiments were carried out (the potential difference between the peaks of the AC voltage was made about 4.8 to 6.3 kV). The results are shown in Table 2a,2b (set forth hereinafter).

As is clear from Table 2a,2b, in the case where the printing of the grid pattern of the surface electrode 5 was performed by changing the pitch from 1.0 mm to 1.5 mm and changing the size of the pointed triangle, when the pitch was small and the distance f between the vertices was small, the amounts of positive ions and negative ions were reduced. On the other hand, the noise value was lowered. This is caused by the fact that one side of the grid square is short, the electric field strength plane is small, and creeping discharges interfere with each other, and therefore stable generation of positive ions and negative ions can not be performed.

On the contrary, when the pitch is large and the distance f between the vertices is large, a large amount of positive ions and negative ions are generated, and accordingly the noise value increases. Thus, the lengths of the pitch and the distance f between the vertices establish a proportional relationship with the yields of positive ions and negative ions and the noise value. The inventors of the present application found from the experiments and the experimental data that, when stable ion generation and a reduction in the noise value are taken into consideration, the distance f between the vertices should not be less than 0.25 mm but not be more than 0.5 mm, and preferably be 0.35 mm as in the prototype (3), while the pitch should not be less than 1.0 mm but not be more than 1.5 mm, and preferably be 1.2 mm as in the prototype (3).

Finally, experiments were performed about an ion generating element 1 comprising the surface electrode 5 having a quadrangle configuration (see FIG. 6), under the same conditions as in the above-mentioned experiments. Note that, in a prototype (8), the pitch was 1.2 mm, the distance f between the vertices was 0.5 mm, the length j between the point A and the point D shown in FIG. 6 was 0.15 mm, and the length k between the point E and the point D was 0.3 mm. The results are shown in Table 3a,3b (set forth hereinafter).

As is clear from Table 3b, the results were as good as those of the prototypes (2) and (3), and stable ion generation was recognized in a wide range of voltage. The noise value was slightly higher, and it was caused as the distance f between the vertices inside the grid square was larger and the electric field was stronger. Note that it is conjectured that the noise problem can be solved by decreasing the distance f between the vertices.

As described in detail above, according to the present invention, on a surface of the dielectric body, in addition to the grid-like surface electrode, the pointed surface electrode is further formed inside the grid squares. More specifically, a triangle having two arbitrary points on a side of the grid square and an arbitrary point inside the grid square as the vertices, or a quadrangle having a crossing of grid lines, an arbitrary point near a straight line connecting crossings of grid lines in the diagonal positions, and two arbitrary points on sides of the grid square as the vertices is formed as an extended part. Accordingly, by further providing the surface electrode with the pointed parts, it is possible to generate positive ions and negative ions in a stable manner in a wide range of voltage application. Consequently, ion generation at a low voltage becomes possible, and further noise and the generation of ozone can be effectively reduced by decreasing the voltage. Since the present invention can generate ions in a stable manner without particularly depending on the strength of the applied voltage, the present invention can give advantageous effects that the ion generating element of the present invention can be incorporated in many apparatuses regardless of the types of apparatuses and conditions of use such as home use and business use.

TABLE 1a

|  | | GRID SQUARE | | MOUNT SHAPE | | |
| --- | --- | --- | --- | --- | --- | --- |
|  | PITCH | NUMBER IN WIDTH | NUMBER IN LENGTH | WIDTH g | HEIGHT h | DISTANCE BETWEEN VERTICES f |
| PROTOTYPE (2) | 1.5 | 19 (=28.5 mm) | 7 (=10.5 mm) | 0.45 | 0.45 | 0.35 |
| PROTOTYPE (3) | 1.2 | 23 (=27.6 mm) | 9 (=10.8 mm) | 0.35 | 0.3 | 0.35 |
| PROTOTYPE (7) | 0.8 | 35 (=28.0 mm) | 13 (=10.4 mm) | SIMPLE GRID | | |

TABLE 1b

|  | INPUT VOLTAGE (AC:V) | HIGH VOLTAGE (kVp-p) | POSITIVE IONS (NUMBER/CC) | NEGATIVE IONS (NUMBER/CC) | NOISE (dBA) | OZONE (ppm) |
| --- | --- | --- | --- | --- | --- | --- |
| PROTOTYPE (2) | 90 | 6.28 | 220000 | 210000 | 42.1 | 0.002 |
|  | 80 | 5.56 | 200000 | 190000 | 39.5 | 0.002 |
|  | 70 | 5 | 160000 | 150000 | 33.4 | 0.003 |
| PROTOTYPE (3) | 90 | 6.2 | 200000 | 200000 | 39.9 | 0.001 |
|  | 80 | 5.6 | 190000 | 180000 | 36.7 | 0.001 |
|  | 70 | 4.96 | 150000 | 130000 | 32.1 | 0.002 |
| PROTOTYPE (7) | 90 | 6.3 | 220000 | 200000 | 41 | 0.003 |
|  | 80 | 5.6 | 190000 | 180000 | 37.4 | 0.002 |

TABLE 2a

|  | | GRID SQUARE | | MOUNT SHAPE | | |
| --- | --- | --- | --- | --- | --- | --- |
|  | PITCH | NUMBER IN WIDTH | NUMBER IN LENGTH | WIDTH g | HEIGHT h | DISTANCE BETWEEN VERTICES f |
| PROTOTYPE (1) | 1.5 | 19 (=28.5 mm) | 7 (=10.5 mm) | 0.45 | 0.35 | 0.5 |
| PROTOTYPE (2) | 1.5 |  |  | 0.45 | 0.45 | 0.35 |
| PROTOTYPE (3) | 1.2 | 23 (=27.6 mm) | 9 (=10.8 mm) | 0.35 | 0.3 | 0.35 |
| PROTOTYPE (4) | 1.2 |  |  | 0.35 | 0.35 | 0.25 |
| PROTOTYPE (5) | 1 | 28 (=28.0 mm) | 10 (=10.9 mm) | 0.25 | 0.25 | 0.25 |

TABLE 2b

|  | INPUT VOLTAGE (AC:V) | HIGH VOLTAGE (kVp-p) | POSITIVE IONS (NUMBER/CC) | NEGATIVE IONS (NUMBER/CC) | NOISE (dBA) |
| --- | --- | --- | --- | --- | --- |
| PROTOTYPE (1) | 90 | 6.16 | 260000 | 230000 | 44 |
|  | 80 | 5.6 | 230000 | 220000 | 41.8 |
|  | 70 | 4.84 | 200000 | 200000 | 40 |

TABLE 2b-continued

|  | INPUT VOLTAGE (AC:V) | HIGH VOLTAGE (kVp-p) | POSITIVE IONS (NUMBER/ CC) | NEGATIVE IONS (NUMBER/ CC) | NOISE (dBA) |
|---|---|---|---|---|---|
| PROTOTYPE (2) | 90 | 6.28 | 230000 | 220000 | 42.1 |
|  | 80 | 5.56 | 200000 | 200000 | 39.5 |
|  | 70 | 5 | 180000 | 180000 | 33.4 |
| PROTOTYPE (3) | 90 | 6.2 | 200000 | 190000 | 39.9 |
|  | 80 | 5.6 | 180000 | 170000 | 36.7 |
|  | 70 | 4.96 | 150000 | 130000 | 32.1 |
| PROTOTYPE (4) | 90 | 6.28 | 200000 | 180000 | 37.2 |
|  | 80 | 5.68 | 160000 | 140000 | 31.1 |
|  | 70 | 5.04 | 60000 | 30000 | 27.2 |
| PROTOTYPE (5) | 90 | 6.32 | 130000 | 130000 | 33.5 |
|  | 80 | 5.68 | 80000 | 90000 | 29.1 |

TABLE 3a

|  | GRID SQUARE | | | MOUNT SHAPE | | |
|---|---|---|---|---|---|---|
|  | PITCH | NUMBER IN WIDTH | NUMBER IN LENGTH | j | k | DISTANCE BETWEEN VERTICES f |
| PROTOTYPE (8) | 1.2 | 23 (=27.6 mm) | 9 (=10.8 mm) | 0.15 | 0.3 | 0.5 |

TABLE 3b

|  | INPUT VOLTAGE (AC:V) | HIGH VOLTAGE (kVp-p) | POSITIVE IONS (NUMBER/ CC) | NEGATIVE IONS (NUMBER/ CC) | NOISE (dBA) |
|---|---|---|---|---|---|
| PROTOTYPE (8) | 90 | 6.24 | 220000 | 220000 | 42.8 |
|  | 80 | 5.56 | 210000 | 210000 | 40.6 |
|  | 70 | 4.8 | 190000 | 190000 | 38.3 |

The invention claimed is:

1. An ion generating element, comprising;
a dielectric body;
an inner electrode formed inside said dielectric body; and
a surface electrode formed on a surface of said dielectric body,
wherein said surface electrode is formed in a grid pattern including a plurality of grid units, at least one side of each grid unit having a pointed part, the pointed part laying in a horizontal plane.

2. The ion generating element as set forth in claim 1, wherein said pointed part is a triangle whose vertices are two arbitrary points on said at least one side of the grid unit and an arbitrary point inside the grid unit.

3. The ion generating element as set forth in claim 2, wherein a plurality of triangles are formed for each grid unit, and a distance between the vertices of the triangles inside the grid unit is not less than 0.25 mm but not more than 0.5 mm.

4. The ion generating element as set forth in claim 1, wherein said pointed part is a quadrangle whose vertices are a crossing of grid lines, an arbitrary point near a straight line connecting crossings of grid lines in diagonal positions, and two arbitrary points on sides of the grid unit.

5. The ion generating element as set forth in any one of claims 1 through 4, wherein a pitch of the grid unit is not less than 1.0 mm but not more than 1.5 mm.

6. The ion generating element as set forth in any one of claims 1 through 4,
wherein said dielectric body has a plate shape, and
said inner electrode lies inside the extent of said surface electrode.

7. An ion generator, comprising:
an ion generating element as set forth in claim 1; and
a voltage applying circuit for applying a voltage to the surface electrode and the inner electrode of said ion generating element, for generating $H^+(H_2O)_n$ (n is a natural number) and $O_2^-(H_2O)_m$ (m is a natural number) in the air by application of a voltage by said voltage applying circuit.

8. An air conditioning apparatus, comprising:
an ion generator having an ion generating element as set forth in claim 1 and a voltage applying circuit for applying a voltage to the surface electrode and the inner electrode of said ion generating element, for generating $H^+(H_2O)_n$ and $O_2^-(H_2O)_m$ in the air by application of a voltage by said voltage applying circuit; and
a blower for sending ions generated by said ion generator to the outside.

9. A cleaner, comprising:
an ion generator having an ion generating element as set forth in claim 1 and a voltage applying circuit for applying a voltage to the surface electrode and the inner electrode of said ion generating element, for generating $H^+(H_2O)_n$ and $O_2^-(H_2O)_m$ in the air by application of a voltage by said voltage applying circuit; and
a blower for sending ions generated by said ion generator out of said cleaner.

10. A refrigerator, comprising:
an ion generator having an ion generating element as set forth in claim 1 and a voltage applying circuit for applying a voltage to the surface electrode and the inner electrode of said ion generating element, for generating $H^+(H_2O)_n$ and $O_2^-(H_2O)_m$ in the air by application of a voltage by said voltage applying circuit; and
a blower for sending ions generated by said ion generator into said refrigerator.

* * * * *